United States Patent

Dysarz

[11] Patent Number: 5,935,113
[45] Date of Patent: Aug. 10, 1999

[54] MODULAR ONE HANDED SAFETY RETRACTABLE NEEDLE CANNULA

[76] Inventor: Edward D. Dysarz, 11423 Triola Ln., Houston, Tex. 77072

[21] Appl. No.: 09/130,968

[22] Filed: Aug. 7, 1998

[51] Int. Cl.[6] .................................................... A61M 5/00
[52] U.S. Cl. ........................... 604/263; 604/192; 604/198
[58] Field of Search .................................... 604/263, 187, 604/192, 195, 198, 110

[56] References Cited

U.S. PATENT DOCUMENTS

| | | |
|---|---|---|
| 3,008,570 | 11/1961 | Roehr et al. . |
| 3,107,785 | 10/1963 | Roehr . |
| 3,306,291 | 2/1967 | Burke . |
| 3,895,633 | 7/1975 | Bartner et al. . |
| 4,300,678 | 11/1981 | Gyure . |
| 4,356,822 | 11/1982 | Winstead . |
| 4,425,120 | 1/1984 | Sampson . |
| 4,466,435 | 8/1984 | Baginetz . |
| 4,655,751 | 4/1987 | Harbaugh . |
| 4,664,654 | 5/1987 | Strauss . |
| 4,702,738 | 10/1987 | Spencer . |
| 4,894,055 | 1/1990 | Sudnak ..................................... 604/198 |
| 4,946,446 | 8/1990 | Vadher ................................. 604/263 X |
| 5,246,428 | 9/1993 | Falknor ................................. 604/263 X |

Primary Examiner—John D. Yasko

[57] ABSTRACT

A modular safety needle cannula device that can be stored independently from the syringe that it will be used with, wherein when it is to be used the modular safety needle cannula device is attached or fixed to a suitable syringe, used to inject medicament into a body and than the used needle cannula is suitably disposed into an elongated module wherein the needle cannula cannot prick or harm a person. The device is comprised of a hub that is used to attach the device to a standard syringe, a capsule, a slideable piston, a compressed biased spring, a needle cannula that is straight and rigid on the first end and curved or flexible between the first end and the second end and wherein the second end of the needle cannula is fixed to the hub. A trigger or release means holds the slideable piston near the first end of the elongated capsule. After the needle cannula has been used to inject medicament into the body, the trigger or release meanes is pressed, releasing the slideable piston and thereby allowing the compressed spring to thrust the slideable piston toward the second end of the needle cannula thereby crushing the curved and flexible section of the needle cannula between the slideable piston and the second end of the elongated capsule thereby destroying the needle cannula and further encapsulating the point at the first end of the needle cannula in the inside of the elongated capsule thereby preventing an accidental needle prick or injury from the point or the first end of the needle cannula.

7 Claims, 4 Drawing Sheets

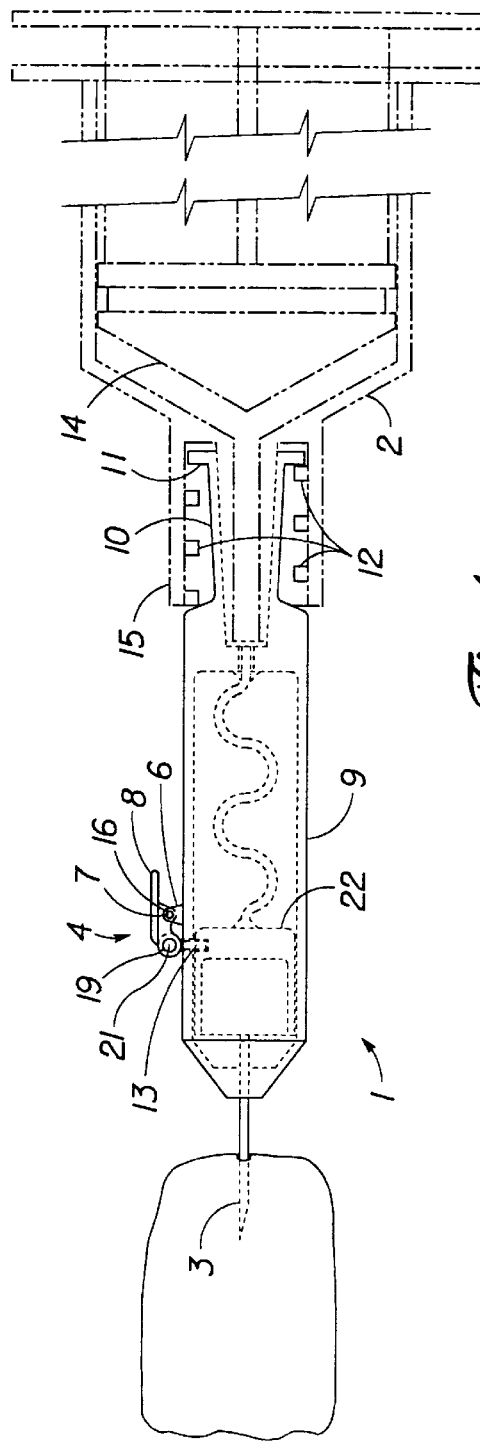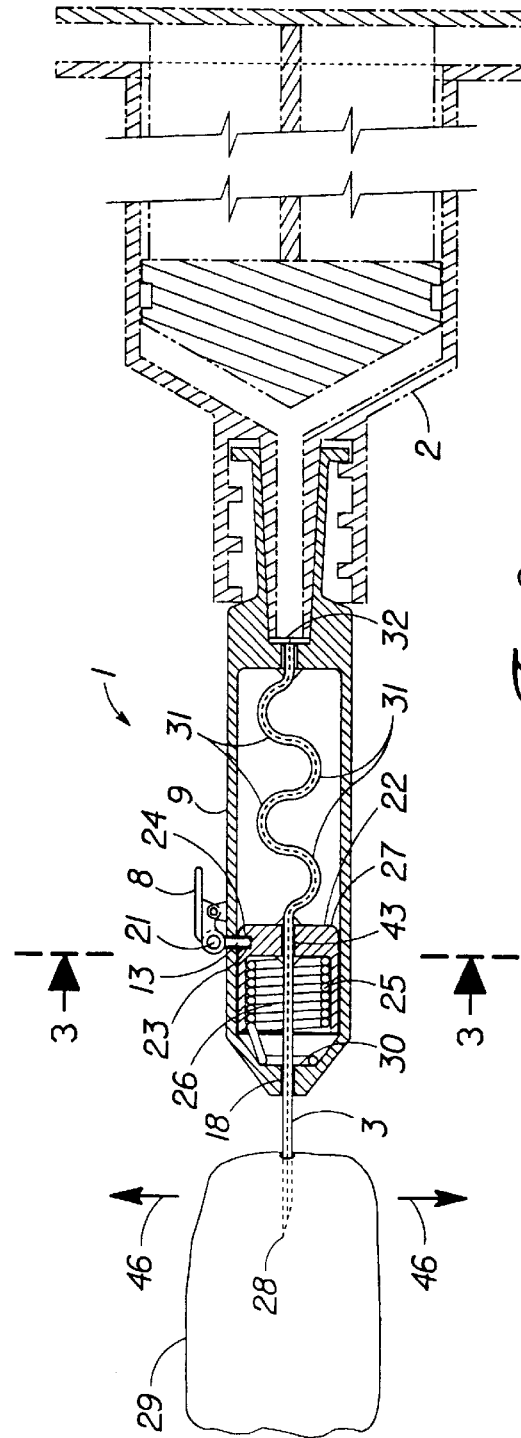

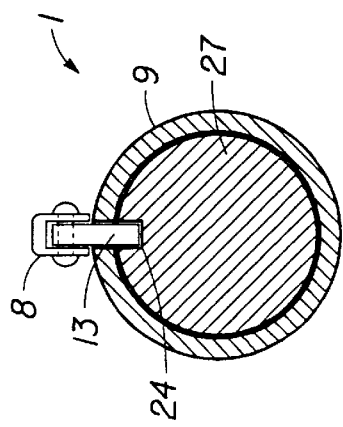
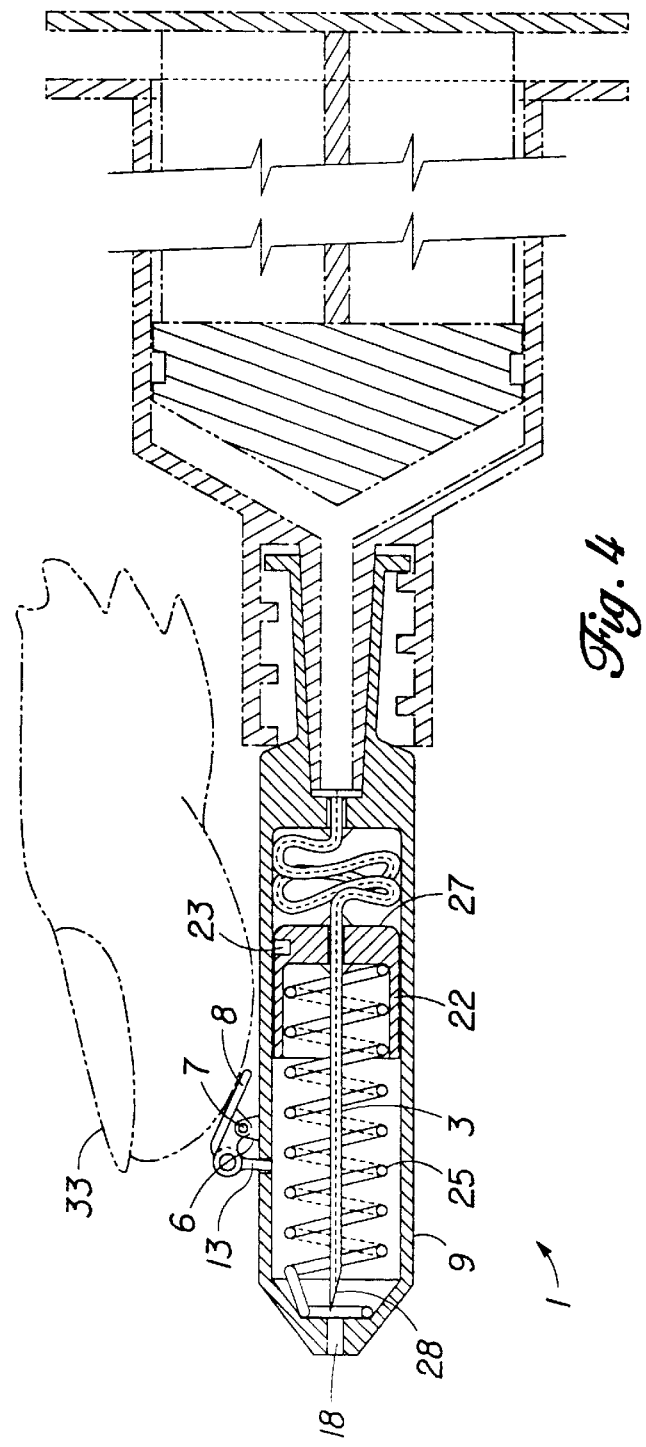

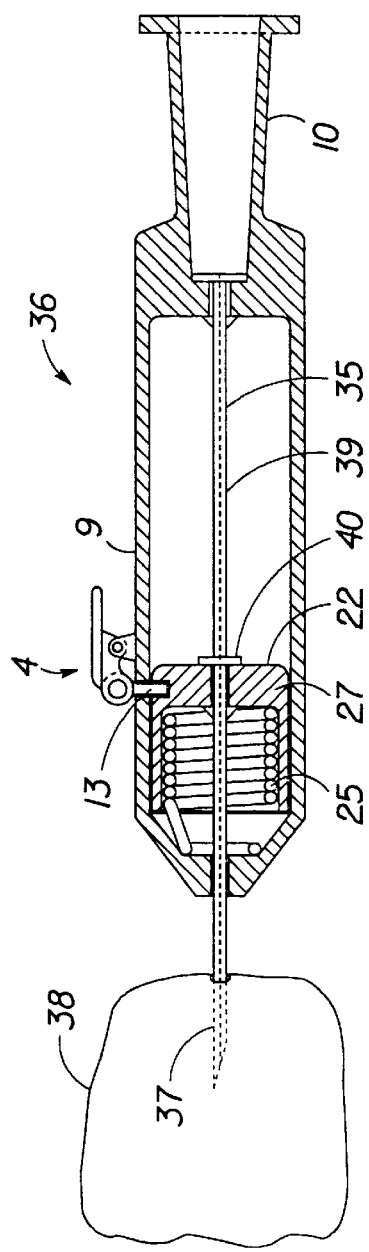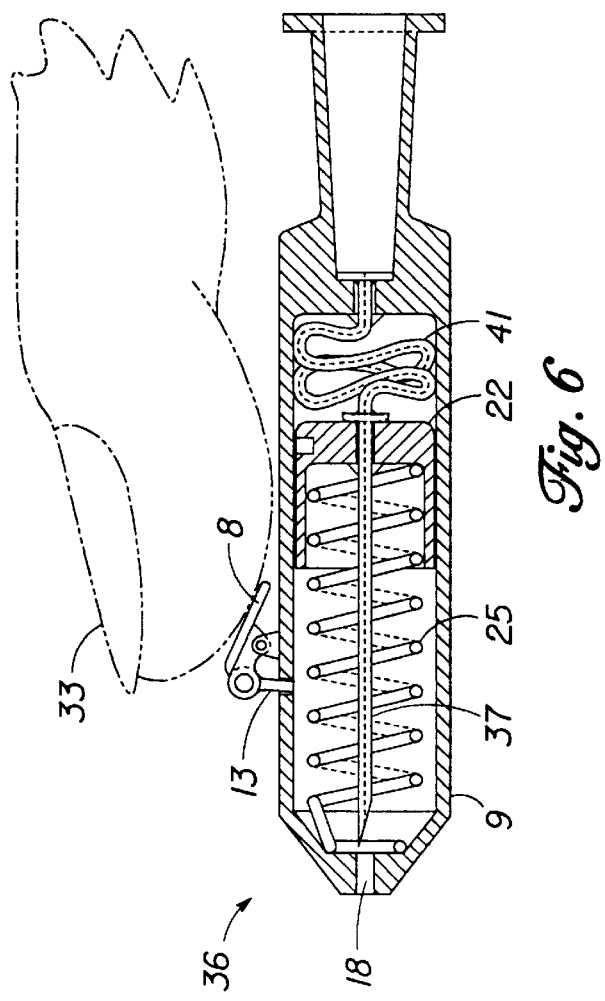

MODULAR ONE HANDED SAFETY RETRACTABLE NEEDLE CANNULA

BACKGROUND OF THE INVENTION

There are many safety syringe designs available today. Some of these designs have a sleeve or sheath that will cover the needle after it has been used. Some typical designs with sleeves or sheaths are Z. M. ROEHR et al U.S. Pat. No. 3,008,570, Z. M. ROEHR U.S. Pat. No. 3,107,785, BARTNER, et al U.S. Pat. No. 3,895,633, G. K. Burke U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 466,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as Weltman U.S. Pat. No. 3,306,290, And DENT U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Both of these designs have one major purpose and that is to prevent the spread of infectious diseases such as aids, hepatitis or other diseases from an accidental injection with a contaminated needle into others after the needle of the syringe was inserted into a patient with the above mentioned diseases. These various designs all work up to a degree, but they all fall short of thier intended purpose during the act of covering the needle, or removing the needle which requires two hands.

All of these designs require at least two hands to operate. The use of two hands to cover the contaminated needle is most unsatisfactory in that during the act of placing a second hand on the syringe the person holding the syringe in one hand may be bumped and accidentaly inject the needle into their other hand before it can grasp the syringe. Other accidental jabbing or injections can happen in an ambulance where just as a person tries to grasp the contaminated syringe, the ambulance can hit a bump in the road causing the person holding the syringe to accidentally stick another person or themselves with the contaminated needle. The need has developed for a syringe that will cover the contaminated needle with the use of only one hand.

All of these designs also combine the needle cannula with the syringe and therefore cause a major inventory and storage problem. At present, needles cannulas are fixed to the hub but are not fixed to the syringe so that a variety of length and guages of needle cannulas are stored in one section which may contain about twenty various lengths and guages of needle cannulas; an inventory of about twenty or more of each guage and length of needle cannula may be stored in each section. There may be about ten sizes of syringes with about twenty or more of each syringe stored in a different section of the same locker. When a given quantity of a given medicament is required, the required size of needle cannula is fitted to the required syringe thereby combining the right length and guage of needle cannula with the right size of syringe.

All of the above mentioned safety syringe needle cannula inventions would require an inventory of about ten (10) times that of the present invention. Each needle cannula size would have to be fixed to each syringe size and each syringe size would have to be fixed to each needle cannula size and this would require an inventory of over a hundred needle cannula syringe combinations which would be multiplied by ten each; the numbers required for the necessary inventory on a given floor of a hospital would be astronomical. The need has developed for a safety needle cannula that will be a module apart from the syringe, that could be placed on any standard syringe.

SUMMARY

It is the object of the present invention to provide a modularized retractable neeedle cannula that is not a part of the syringe system but that can be suitably fixed to various syringes of various sizes.

It is another object of the present invention to provide a safety retractable needle cannula wherein the needle cannula will retract into a module or capsule that can be attached or removed from a common syringe.

It is yet another object of the present invention to provide a one handed retractable safety syringe.

It is still yet another object of the present invention to provide a safety needle cannula that will not come out of the capsule after the needle cannula has been retracted into the capsule.

The foregoing and other object and advantages are attained by a module comprised of a hub, a needle cannula with a rigid first end a saft or flexible second end suitably fixed to said hub, a capsule a slideable piston, with a biased spring inside of said capsule and a release means wherein the module is fixed to any necessary size of syringe, and wherein a medicament is injected into a body with the needle cannula, the needle cannula is then withdrawn from said body and said release means releases said slideable piston and said biased spring thereby thrusting said needle cannula into said capsule wherein the tip of said needle cannula is contained in said module or capsule, wherein the tip of said needle cannula is contained in said module or capsule.

The features of the present invention can be best understood together with further objects and advantages by reference to the following descriptions taken in conjuntion with accompanying drawings, wherein like numerals indicate like parts.

BRIEF DESCRIPTION OF THE DRAWINGS

FIG. 1 is an outside elevation of the exterior of the device attached to a syringe.

FIG. 2 is a section elevation of the device attached to a syringe.

FIG. 3 is a section view of the release means as taken trough FIG. 2.

FIG. 4 is a section elevation of the device showing the slideable piston crushing the second end of the needle cannula.

FIG. 5 is a section elevation of the device of the second perferred embodiments showing a composite needle cannula.

FIG. 6 is a section elevation of the second preferred embodiment showing the second end of the composite needle cannula crushed.

DETAILED DESCRIPTION OF THE PREFERRED EMBODIMENTS

Figure 7:
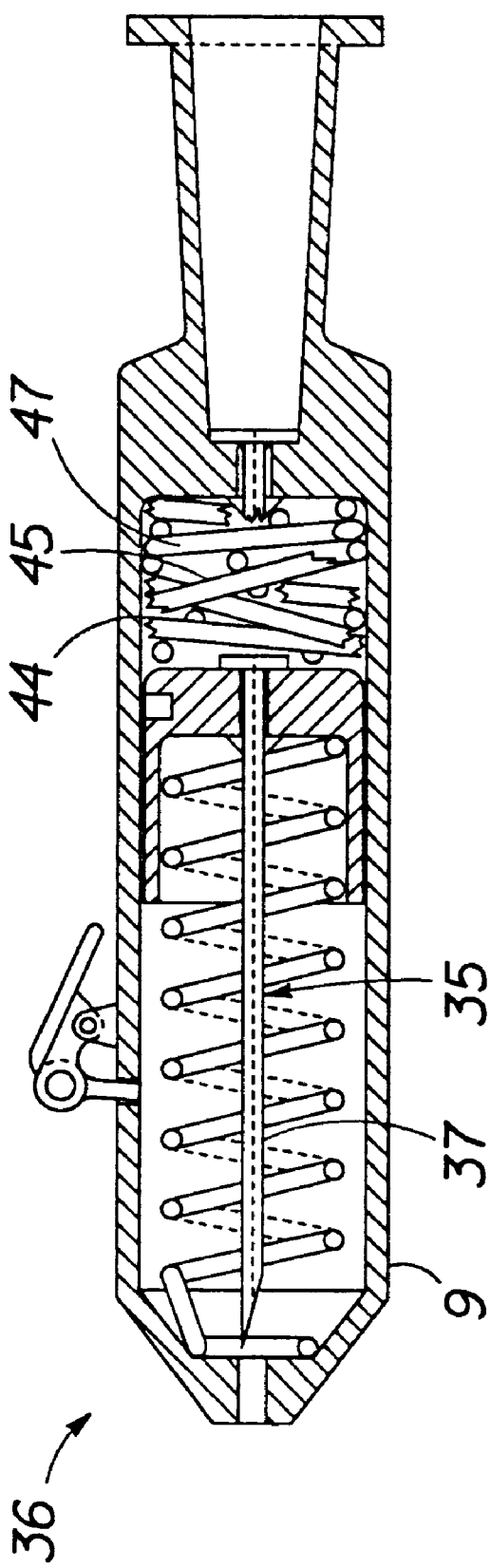
FIG. 7 is a section elevation of the device of the second preferred embodiment showing a glass composite cannula crushed.

Referring to FIG. 1 there is shown an elevation view of the device 1 suitably fixed to a syringe 2.

The first end of the needle cannula 3 is shown extending out of the first end of the elongated capsule 9. The first end of the hub 10 is shown suitably fixed to the second end of the elongated capsule 9. The second end of the hub 10 is shown suitably fixed to the first end of the threaded lock 11. The second end of the threaded lock 11 is near the plunger 14 of the syringe 2. The threaded lock 11 is shown suitably fixed to the internal threads 12 of the threaded extension 15 which is part of the syringe 2. The threaded extension 15 and the internal threads 12 are a standard connection for needles as they are manufactured and sold at the present time. The hub 10 and the threaded lock 11 would all be a standard size of the device that holds a conventional needle cannula. The threaded extension 15 the hub 10 and the threaded lock could also be a conventional slip on friction connector or an eccentric connection or a catheter type of connection by design choice. The hub 10 is shown with an inside and an outside that would attach to any desired syringe of any size.

A latch means 4 is shown suitably fixed to the outside of the elongated capsule 9. The latch means 4 is comprised of two fulcrums 6 each with a first end that is suitably fixed to the outside surface of the elongated capsule 9. A first hole 16 is formed near the second end of each fulcrum 6 wherein a fulcrum pin 7 is inserted through each first hole 16 wherein the fulcrum pin 7 is fixed to each fulcrum 6. A latch bar 8 is shown with a first end and a second end and a second hole is formed in said latch bar 8 that extends from the first side to the second side of said latch bar 8 wherein said fulcrum pin 7 is disposed in said second hole thereby allowing said latch bar 8 to rotate about said fulcrum pin 7. A third hole 19 is formed at the first end of latch bar 8 wherein said third hole 19 extends from the first side to the second side of said latch bar 8. A piston stop 13 is shown suitably fixed to said latch bar 8 by a piston stop pin 21. The piston stop pin 21 extends from the first side of the latch bar 8, through a fourth hole formed in the piston stop 13 and to the second side of the latch bar 8. The piston stop 13 extends from the latch bar 8, through a hole formed in the elongated capsule 9 that extends from the outside to the inside of the elongated capsule 9. The piston stop 13 further extends into a piston 22 that is disposed within the elongated capsule 9. The piston stop 13, prevents the piston from moving or being moved until the piston stop 13 is removed from the piston 22. Although the device 1 is not shown in a package or with caps, the device 1 will be stored, shipped and generally kept in a seperate package apart from the syringe 2. The device 1 will be suitably fastened to the appropriate syringe prior to use.

Referring to FIG. 2 there is shown is shown a section elevation of the device 1 attached to a syringe 2.

The first end of the piston stop 13 is shown rotatably fixed to the first end of the latch bar 8 by the piston stop pin 21. The piston stop 13 is shown extending through the piston stop hole 23 that extends from the outside surface of the elongated capsule 9 to the inside surface of the elongated capsule 9 wherein the second end of the piston stop 13 is disposed in the piston hole 24 formed near the second end of the piston 22. The piston stop 13 prevents the piston 22 from moving or being moved longitudeinally within the elongated capsule 9.

A biased spring 25 is shown compressed within the piston cavity 26. The piston cavity 26 has a first end near the first end of the elongated capsule 9 and the second end of the piston cavity 26 is fixed to the first end of the piston base 27. The piston cavity has an outside surface and an inside surface. The biased spring 25 is thrusting on the first end of the piston base 27 but is restrained by the piston stop 13. The needle cannula 3 is shown with a point 28 on the first end. The needle cannula 3 extends into the elongated capsule 9 through a needle cannula tunnel 18 that is formed in the first end of the elongated capsule. The needle cannula tunnel 18 provides lateral stability for the needle cannula 3 as the needle cannula is being injected into a body 29 or part of a body. The needle cannula tunnel will also prevent the needle cannula 3 from moving latteraly 46 as the needle cannula 3 is being withdrawn into the inside of the elongated capsule 9 or as the needle cannula 3 is being injected into a body 29.

The first end of the biased spring 25 is shown thrusting on the first capsule flat 30 that is formed on the inside on the first end of the elongated capsule 9. The second end of the biased spring 25 is thrusting on the first side of the piston base 27. The second end of the biased spring 25 is shown contained in the cavity 26 formed in the piston 22. The cavity 26 is shown with an inside surface and an outside surface, a first end near the first capsule flat 30 and a second end at the piston base 27.

The needle cannula 3 is shown extending through the piston 22 and through a base hole 43 formed in the piston base 27 that extends from the first end of the piston base 27 through the second end of the piston base 27 wherein the needle cannula 3 is suitably fixed to the piston base 27 that is at the second end of the piston 22. The needle cannula is shown with at least one needle cannula arc 31 that will enable the needle cannula 3 to colapse upon itself as will be shown in FIG. 4. The second end of the needle cannula 3 is shown suitably fixed to the first side of a flange 32 and wherein the second side of the flange 32 could be pressed against an internal part of the syringe 2 to provide a high pressure fluid tight connection between the needle cannula 3 and the syringe 2 or in any conventional method of providing a high pressure fluid tight connection between a needle cannula 3 and a syringe 2 by design choice.

As medicament or other fluid is forced from the syringe 2 into the needle cannula 3, the fluid will travel from the syringe 2 into the needle cannula 3 past or through the flange 32 through the needle cannula arc 31 or arcs, through the first end of the needle cannula 3 and into a body 29.

Although there are no joints shown formed in the elongated capsule 9 wherein the needle cannula 3, the piston 22 and the biased spring 25 are to be placed on the inside of the elongated capsule 9 it will be by design choice that a suitable means of entery will be provided on the elongated capsule 9 for necessary and propper assembly of the device 1.

Referring to FIG. 3 there is shown a section elevation of the device 1 as taken through FIG. 2.

The piston base 27 is shown with the piston stop 13 suitably disposed in the piston hole 24. The piston stop 13 is shown rotatably fixed to the latch bar 8. The inside surface and the outside surface of the elongated capsule 9 are shown.

Referring to FIG. 4 there is shown a section elevation of the device 1 during or after the piston 22 has been released.

A finger 33 has pressed downward on the second end of the latch bar 8 thereby rotating the latch bar 8 about the fulcrum pin 7 and further causing the latch bar 8 to pull the piston stop 13 out of the piston hole 23 formed in the piston base 27 of the piston 22 thereby releasing the piston 22 wherein the biased spring 25 is allowed to thrust the piston 22 and the piston base 27 toward the second end of the elongated capsule 9 thereby crushing the needle cannula arc section of the needle cannula 3 into the inside second end of the elongated capsule 9. As the piston 22 crushes the second end of the needle cannula 3, the first end of the needle cannula 3 and the point 28 of the needle cannula 3, are withdrawn through the needle cannula tunnel 18 and into the inside of the elongated capsule 9 where the point 28 is completly sheltered and therefore cannot prick or othewise injure others by spreading bacteria or germs. The biased spring 25 will also keep a constant pressure on the piston 22 thereby preventing the point 28 of the needle cannula 3 from falling out of the inside of the elongated capsule 9. The needle cannula 3 is also completly destroyed.

Referring to FIG. 5 there is shown a second device 36 of the second preferred embodiment with a composite needle cannula 35.

The elongated capsule 9, the latch means 4, the piston 22, the biased spring 25, the hub 4 and the piston stop 13 are all the same as shown in FIG. 1, FIG. 2, FIG. 3 and FIG. 4; only the composite needle cannula 35 is different from the needle cannula of the first preferred embodiment.

The first end of the composite needle cannula 35 is a hard needle cannula 37 made out of a suitable material such as steel or even hard plastic if it is possible to penetrate the skin of a body 38. The second end of the composite needle cannula 35 is made out of a flexable or bendable material such as plastic or bendable metal tubing that can contain medicament under high pressure but will be latteraly bendable. The bendable cannula 39 is shown suitably fixed to the hard needle cannula 37 near the joint flange 40. The connection of the hard needle cannula 37 and the bendable cannula 39 could be inside of the piston base 27 or at the first end of the piston base 27 by design choice. The bendable material could also be crushable material such as glass, a hard plastic or a brittle metal.

Referring to FIG. 6 there is shown a section elevation of the second device 36 of the second preferred embodiment.

A finger 33 or a thumb has depressed the latch bar 8 thereby pulling up on the piston stop 13, further releasing the piston 22 allowing the biased spring 25 to thrust the piston 22 into the inside second end of the elongated capsule 9 thereby compressing the bendable cannula 39 into a bendable cannula pile 41. The hard needle cannula 37 has been withdrawn past the needle cannula tunnel 18 into the inside of the elongated capsule wherein the hard needle cannula cannot prick a person or otherwise spread an infectious disease such as aids or hepatitis or other diseases.

Referring to FIG. 7 there is shown a section elevation of the second device 36 of the second preferred embodiment wherein the second end of the composite needle cannula 35 is made out of glass or another suitable material wherein the crushable cannula 47 has been shattered into a brittle cannula pile 44.

The hollow glass cannula 45 is shown broken into many pieces of glass particules that cannot be repaired or reused. The device has now been rendered useless and the hard needle cannula 37 has been withdrawn into the elongated capsule 9 wherein it cannot prick another person.

Although the system described in detail supra has been found to be most satisfactory and preferred, many variations are possible. For example, the latching means could be anothers design or there could be two or more latch means, the device could be a slip lock connection for the syringe.

Although the invention has been described with reference to the preferred embodiment, it will be understood by those skilled in the art, that additions, modifications, substitutions, deletions and other changes not specifically described, may be made in the embodiments wherein, it should be understood that the details herein are to be interpreted as illustrative and are not in a limiting sense.

What is claimed as invention:

1. A modular one handed safety retractable needle cannula device that is attached to a syringe and could be removed from said syringe wherein said modular one handed safety retractable needle cannula is used to inject medicament or fluid from said syringe into a body comprising;

an elongated capsule with a first end, a second end, an inside and an outside wherein a needle cannula tunnel is formed in said first end of said elongated capsule and wherein said needle cannula tunnel extends from said outside to said elongated capsule to said inside of said elongated capsule and wherein said elongated capsule has a piston stop hole formed near said first end of said elongated capsule and wherein said piston stop hole extends from said inside to said outside of said elongated capsule;

a piston with a first end and a second end an inside surface and an outside surface wherein said piston is comprised a hollow first end and a piston base formed at said second end wherein said piston base has a first side, a second side and an outside and wherein a cannula hole is formed in said piston base and wherein said cannula hole extends from said first side to said second side to said piston base and wherein a piston stop hole is also formed on said outside of said piston base;

a biased spring with a first end and a second end wherein said first end of said biased spring is thrusting against said inside of said first end of said elongated capsule and wherein said second end of said biased spring is disposed in said hollow first end of said piston and said second end of said biased spring is thrusting against said first side of said piston base;

a latch means wherein said latch means is comprised of a latch bar with a first end and a second end and a piston stop with a first end and a second end wherein said first end of said piston stop is rotatably fixed to said latch bar and wherein said second end of said piston stop extends through said piston stop hole formed in said piston base and wherein said piston stop prevents said biased spring from thrusting said piston and piston base into said second end of said elongated capsule;

a needle cannula with a first end and a second end wherein said first end of said needle cannula extends from said cannula tunnel formed in said first end of said elongated module and wherein said needle cannula is further disposed in said cannula hole formed in said psiton base and wherein said needle cannula is further fixed to said piston base and wherein at least one arc is formed in said needle cannula between said piston base and said second end of said needle cannula and wherein said second end of said needle cannula is fixed to said second end of said elongated capsule;

a hub with a first end and a second end wherein said first end of said hub is fixed to said second end of said elongated capsule and wherein said hub has an inside and an outside and wherein said hub, said elongated capsule and said needle cannula comprise most of said device and wherein said device may be stored in a place apart from said syringe and wherein said device is joined at said hub to said yringe of a desired size and wherein said syringe is filled with a desired measurement of said medicament, and wherein said needle cannula is injected into a body and wherein said medicament is further injected into said body from said syringe through said needle cannula, and wherein when all of said medicament has been injected into said body, said needle cannula may be removed from said body and disposed inside of said elongated capsule by pressing on said second end of said latch bar wherein said first end of said latch bar that is rotatably attached to said first end of said piston stop pulls said piston stop from said piston hole formed in said piston base thus releasing said piston and further allowing said biased spring to thrust said piston into said inside second end of said elongated capsule thereby withdrawing said first end of said needle cannula through said cannula tunnel and into said inside of said elongated capsule thereby sheltering and covering said first end of needle cannula from accidentally pricking or injuring others and wherein said second end of said needle cannula is bent and crushed between said second side of said piston base and said second end of the inside of said elongated capsule thereby destroying said needle cannula and rendering said needle cannula useless.

2. The modular one handed safety retractable needle cannula device of claim 1 wherein said hub is fixed to the first end of a threaded lock and wherein said threaded lock is threaded onto a threaded extension of said syringe.

3. The modular one handed safety retractable needle cannula device of claim 1 wherein said second end of said needle cannula is fixed to said first end of a flange.

4. A modular one handed safety retractable needle cannula device that is attached to a syringe and could be removed from said syringe wherein said modular one handed safety retractable needle cannula is used to inject medicament or fluid from said syringe into a body comprising;

an elongated capsule with a first end, a second end, an inside and an outside wherein a needle cannula tunnel is formed in said first end of said elongated capsule and wherein said needle cannula tunnel extends from said outside to said elongated capsule to said inside of said elongated capsule and wherein said elongated capsule has a piston stop hole formed near said first end of said elongated capsule and wherein said piston stop hole extends from said inside to said outside of said elongated capsule;

a piston with a first end and a second end an inside surface and an outside surface wherein said piston is comprised a hollow first end and a piston base formed at said second end wherein said piston base has a first side, a second side and an outside and wherein a cannula hole is formed in said piston base and wherein said cannula hole extends from said first side to said second side to said piston base and wherein a piston stop hole is also formed on said outside of said piston base;

a biased spring with a first end and a second end wherein said first end of said biased spring is thrusting against said inside of said first end of said elongated capsule and wherein said second end of said biased spring is disposed in said hollow first end of said piston and said second end of said biased spring is thrusting against said first side of said piston base;

a latch means wherein said latch means is comprised of a latch bar with a first end and a second end and a piston stop with a first end and a second end wherein said first end of said piston stop is rotatably fixed to said latch bar and wherein said second end of said piston stop extends through said piston stop hole formed in said piston base and wherein said piston stop prevents said biased spring from thrusting said piston and piston base into said second end of said elongated capsule;

a composite needle cannula with a first end and a second end wherein said first end of said composite needle cannula is a hard needle cannula with a first end and a second end and wherein said second end of said composite needle cannula is a bendable cannula with a first end and a second end wherein said first end of said hard needle cannula extends from said cannula tunnel formed in said first end of said elongated module and wherein said second end of said hard needle cannula is further disposed in said cannula hole formed in said piston base and wherein said second end of said hard needle cannula is further fixed to said piston base and wherein said second end of said hard needle cannula is also fixed to said first end of said bendable cannula and wherein said bendable cannula has a second end that is fixed to second end of said elongated capsule;

a hub with a first end and a second end wherein said first end of said hub is fixed to said second end of said elongated capsule and wherein said hub has an inside and an outside and wherein said hub, said elongated capsule and said composite needle cannula comprise most of said device and wherein said device may be stored in a place apart from said syringe and wherein said device is joined at said hub to said syringe of a desired size and wherein said syringe is filled with a desired measurement of said medicament, and wherein said hard needle cannula is injected into a body and wherein said medicament is further injected into said body from said syringe through said bendable cannula, and said hard needle cannula and wherein when all of said medicament has been injected into said body, said hard needle cannula may be removed from said body and disposed inside of said elongated capsule by pressing on said second end said latch bar wherein said first end of said latch bar that is rotatably attached to said first end of said piston stop pulls said piston stop from said piston hole formed in said piston base thus releasing said piston and further allowing said biased spring to thrust said piston into said inside second end of said elongated capsule thereby withdrawing said first end of said hard needle cannula through said cannula tunnel and into said inside of said elongated capsule and further crushing said bendable cannula end of said piston base and said second end of said elongated capsule thereby sheltering and covering said first end of said hard needle cannula from accidentally pricking or injuring other and wherein said bendable cannula at said second end of said composite needle cannula is crushed between said second end of said piston base and said second end of the inside of said elongated capsule thereby destroying said composite needle cannula and rendering said composite needle cannula useless.

5. A modular one handed safety retractable needle cannula device of claim 4 wherein said bendable cannula is made out of glass.

6. A modular one handed safety retractable needle cannula device of claims 4 wherein said bendable cannula is made out of plastic.

7. A modular one handed safety retractable needle cannula device of claims 4 wherein said bendable cannula is made out of metal.

* * * * *